United States Patent [19]

Hoffman et al.

[11] Patent Number: 5,599,543
[45] Date of Patent: Feb. 4, 1997

[54] IMMUNOGENIC FOUR AMINO ACID EPITOPE AGAINST *PLASMODIUM VIVAX*

[75] Inventors: Stephen L. Hoffman, Gaithersburg; Yupin Charoenvit, Silver Spring, both of Md.; Trevor R. Jones, Brooklyn, Conn.

[73] Assignee: The United States of America as represented by the Secretary of the Navy, Washington, D.C.

[21] Appl. No.: 848,636

[22] Filed: Mar. 9, 1992

Related U.S. Application Data

[63] Continuation-in-part of Ser. No. 609,551, Nov. 6, 1990, Pat. No. 5,095,093.
[51] Int. Cl.$^6$ .................................................. A61K 39/015
[52] U.S. Cl. ............................ 424/191.1; 424/193.1; 424/268.1; 424/272.1; 530/330; 530/403
[58] Field of Search .................................. 424/88, 184.1, 424/191.1, 272.1, 185.1, 268.1; 514/2, 12–18; 530/300, 324–330, 402, 403, 806, 807

[56] References Cited

U.S. PATENT DOCUMENTS

| | | |
|---|---|---|
| 4,466,917 | 8/1984 | Nussenzweig et al. . |
| 4,693,994 | 9/1987 | McCutchan et al. . |
| 4,707,357 | 11/1987 | Dame et al. . |
| 4,826,957 | 5/1989 | Nussenzweig et al. . |
| 4,957,869 | 9/1990 | Arnot et al. . |

OTHER PUBLICATIONS

Collins et al, Am. J. Trop. Med. Hyg., 40(5), 1989, pp. 455–464.

William E. Paul, Fundamental Immunology, Second Edition, 1989, pp. 975–977.

Godson, G. N. Scientific American, May 1985, pp. 52–59. "Molecular approaches to malaria vaccines".

Collins, W. E. et al. Am. J. Trop. Hyg. 40:455–464 (May 1989), "Immunization of *Saimiri sciureus boliviensis* with recombinant vaccines based on the CSP of *P. vivax*".

Malini, R. et al. Med Sci. Res. 17:473–476 (1989) "Chemical synthesis and immunological properties of an immunodominant CS peptide of *P. vivax*".

Cox, F. E. G., Tibtech 9:389–394 (1991), "Malaria vaccines–progress and problems".

Nussensweig, V. et al., Mol. Parasitol. pp. 117–126 (1984), "Protective immunity to malarial sporozoites".

Romero, P. et al., Curr. Opin. Immunol.. 4(4):432–441 (1992), "Malaria vaccines".

Fundamental Immunology, William E. Paul, ed., pp. 975–977 (1989).

*Primary Examiner*—Thomas M. Cunningham
*Attorney, Agent, or Firm*—A. David Spevack; William C. Garvert

[57] ABSTRACT

An agent and pharmaceutical formulations of the agent containing a synthetic peptide of the human malaria *Plasmodium vivax*, containing at least one repeat of a synthetic peptide having the amino acid sequence Ala-Gly-Asp-Arg (AGDR) which is a protective epitope found on the circumsporozoite (CS) protein of the sporozoites of the human malaria *Plasmodium vivax*. When a monoclonal antibody specific for this four amino acid sequence binds to the CS protein of the *P. vivax* sporozoite in vivo, infection is prevented.

12 Claims, No Drawings

IMMUNOGENIC FOUR AMINO ACID EPITOPE AGAINST *PLASMODIUM VIVAX*

BACKGROUND OF THE INVENTION

1. Related Applications

This application is a Continuation-in-Part of U.S. patent application Ser. No. 07/609,551 filed 6 Nov. 1990, now U.S. Pat. No. 5,095,093 issued 10 Mar. 1992.

2. Field of the Invention

This invention relates to a synthetic peptide of the human malaria *Plasmodium vivax*, more particularly the invention relates to a synthetic or recombinant peptide containing the sequence AGDR (SEQ ID NO:1) which is a protective epitope found on the circumsporozoite (CS) protein of the sporozoites of the human malaria *Plasmodium vivax*. When a monoclonal antibody specific for this four amino acid sequence binds to the CS protein of the *P. vivax* sporozoite in vivo, infection is prevented. The peptide and repeats of the peptide cause the formation of antibodies.

DESCRIPTION OF THE PRIOR ART

Of the four human malarias, *P. vivax* and *P. falciparum* are the most common and cause the majority of the malaria-induced disease seen worldwide. Prevention of infection by these human parasites would alleviate a major health problem in the tropical and subtropical areas of the world. The most promising method for the control of malaria appears to be the development and use of vaccines. One approach to malaria vaccine development involves the use of the CS protein as a vaccine antigen. This protein covers the surface of the sporozoite. The sporozoite is the life stage of the parasite which is transmitted to humans by feeding female Anopheline mosquitoes. Evidence from both mouse and human malarias indicates that antibodies to the CS protein can provide protection in vivo against infection by sporozoites (Charoenvit et al., Infect. Immunity, 55:604 (1987); Charoenvit et al., in press, J. Immun. (1991); Charoenvit et al., in press, Science (1990).

In 1985, McCutchan and colleagues sequenced the gene for the CS protein in *P. vivax* and determined the amino acid sequence derived from that gene (McCutchan et al., Science, 230:1381 (1985)). In 1987, McCutchan and Wistar, in U.S. Pat. No. 4,693,994, described a repeated nine amino acid sequence within the CS protein as an immunodominant synthetic peptide. The repeated sequence is Gly-Asp-Arg-Ala-Asp-Gly-Gln-Pro-Ala (SEQ ID NO:2). In the '994 patent and in other publications, McCutchan/Wistar maintain that the nine amino acid sequence is capable of inducing antibodies protective against *P. vivax* malaria. Experimental evidence indicates that while the McCutchan/Wistar sequence stimulates the development of anti-CS antibody in humans, it is not capable of inducing protective antibodies. In an article published in Am. J. Trop. Med. Hyg. 40(5):455–464 (1989), Collins et al. describes tests in which Saimiri monkeys (*Saimiri sciureus boliviensis*), which are susceptible to human vivax malaria, were immunized with two different preparations (VIVAX-1 and NS1$_{81}$V$_{20}$). Both preparations contain the McCutchan/Wistar peptide (Gly-Asp-Arg-Ala-Asp-Gly-Gln-Pro-Ala) (SEQ ID NO:2). When these monkeys were challenged with 10$^4$ *P. vivax* sporozoites, there was no significant protection.

Nussenzweig et al., in U.S. Pat. No. 4,826,957, describes an immunogenic recombinant yeast expression product which contains a long sequence incorporating a portion of the *P. vivax* circumsporozoite. The sequence contains multiple repeats of the sequence Gly-Asp-Arg-Ala-Asp-Gly-Gln-Pro-Ala (SEQ ID NO:2) as part of a complex polypeptide. The vaccine causes the formation of antibodies, to Gly-Asp-Arg-Ala-Asp-Gly-Gln-Pro-Ala (SEQ ID NO:2), but does not provide consistent protection against challenge with malaria sporozoites. There is a need for a simple material to generate a vaccine against *P. vivax*.

SUMMARY OF THE INVENTION

Accordingly, it is an object of this invention to characterize the nature of a protective epitope found within the amino acid sequence of the CS protein of *P. vivax*.

It is a further object of the present invention to provide a synthetic peptide that causes the formation of antibodies that will form the basis of a synthetic vaccine capable of inducing antibodies protective against infection caused by the sporozoites of *P. vivax*.

Another object of the invention is an immunogenic peptide incorporated in an anti-malarial vaccine preparation.

An additional object of the invention is a method of causing the formation of antibodies which will immunize against malaria caused by *P. vivax*.

Yet another object of the invention is a vaccine protective against malaria caused by *P. vivax*.

Other objects and advantages of this invention will become clear as the detailed description of the present invention is presented.

These and additional objects of the invention are accomplished by at least one repeat of a synthetic peptide having the amino acid sequence Ala-Gly-Asp-Arg (AGDR) (SEQ ID NO:1) and pharmaceutical formulations of these peptides.

DESCRIPTION OF THE PREFERRED EMBODIMENTS

The monoclonal antibody originally used by McCutchan and colleagues (McCutchan et al., Science, 230:1381 (1985)) to isolate the protein and the nucleotide sequence which later became the subject of the McCutchan/Wistar U.S. Pat. No. 4,693,994 was originally developed by Charoenvit and Beaudoin of the Infectious Diseases Department, Naval Medical Research Institute (NMRI). It was used at NMRI as a passive immunization agent. Saimiri monkeys were immunized by the intravenous infusion of 2 mg per animal of the monoclonal antibody (designated NVS3— produced by a hybriduma cell line deposited at the American Type Culture Collection, 12301 Parklawn Drive, Rockville, Md. 29862, U.S.A. as ATTC designation HB10615) then challenged with 10$^4$ *P. vivax* sporozoites injected intravenously. Four of six animals were completely protected and the remaining two experienced a significant delay in the onset of disease. These findings are the subject of a concurrently filed application filed in the name of Charoenvit et al. and titled "NVS3 as a Passive Protective Agent Against *P. vivax*." Analysis of this protective antibody by epitope scanning technology revealed that NVS3 has as its specific epitope the amino acid sequence alanine-glycine-aspartic acid-arginine (Ala-Gly-Asp-Arg, otherwise abbreviated as AGDR) (SEQ ID NO:1). Through subsequent work, it was surprising to find that circulating antibodies against the epitope AGDR (SEQ ID NO:1) protect against infection by *P. vivax* sporozoites and hence AGDR (SEQ ID NO:1) is immunogenic.

The analysis of serum samples from humans and Saimiri monkeys vaccinated with a vaccine, $NS1_{81}V_{20}$, containing the McCutchan/Wistar sequence (Gly-Asp-Arg-Ala-Asp-Gly-Gln-Pro-Ala, also abbreviated as GDRADGQPA) (SEQ ID NO:2), which contains the amino acids Alanine, Glycine, Aspartic acid, and Arginine, revealed that both the humans and monkeys generated antibodies that bound to *P. vivax* sporozoites and to the McCutchan/Wistar sequence, but no antibodies could be detected to the protective epitope AGDR (SEQ ID NO:1). As noted by Collins et al., this vaccine did not produce statistically significant protection against *P. vivax* malaria. This lack of protection is surprising because Alanine is the last acid in the McCutchan/Wistar sequence and Glycine, Aspartic acid and Arginine are the first acids in the series of the McCutchan/Wistar sequence, therefore the McCutchan/Wistar sequence contains the AGDR (SEQ ID NO:1) sequence when there is more than one repeat, and the vaccine $NS1_{81}V_{20}$ contained multiple copies of AGDR (SEQ ID NO:1).

The present invention rests on the discovery of an amino acid sequence within the CS protein which is the epitope of monoclonal antibodies which protect against sporozoite-induced *P. vivax* malaria. The knowledge that this amino acid sequence is the epitope of an antibody which prevents infection with *P. vivax* malaria, allows the design of synthetic or recombinant proteins based on this amino acid sequence which can be used as vaccines.

Failure of vaccines already containing the protective epitope AGDR (SEQ ID NO:1) to induce a protective antibody response indicates that the presentation of AGDR (SEQ ID NO:1)-based vaccines is important. These vaccines should not contain the extraneous amino acids from the McCutchan/Wistar sequence. The simplest embodiment of the invention is the peptide AGDR (SEQ ID NO:1). In another embodiment the AGDR (SEQ ID NO:1) sequence is a simple chains of repeating AGDR (SEQ ID NO:1) sequences. The exact number of repeats is not critical. Up to about thirty repeats is preferred. In yet another embodiment, the peptide for the vaccine is formed as simple chains containing AGDR (SEQ ID NO:1) sequences separated by spacer sequences. Again, the number of repeats or the number of spacers is not critical except that care must be taken to avoid creating the hindrances which must be present in the McCutchan/Wistar sequence. The spacers can separate single or multiple repeats of the AGDR (SEQ ID NO:1) sequence. MAPS (multiple antigenic peptide systems) can be formed by conjugating multiple AGDR (SEQ ID NO:1) containing chains to a central moiety. These MAPS are described by Tam et al., PNAS USA 86:9084 (1989). Combinations of these several forms are considered part of the invention.

To be used as vaccines, these AGDR (SEQ ID NO:1)-based peptides can be linked to a carrier protein which may or may not contain a T-cell epitope which may or may not be of malarial origin. This peptide/carrier combination then may be delivered in conjunction with delivery systems and adjuvants including but not exclusive of aluminum hydroxide, liposomes, monophosphoryl lipid A and Mycobacterium components.

It is noted that those technical terms or phrases used here which have not been specifically defined have the same meaning as generally understood by one of ordinary skill in the art to which this invention belongs. The term "synthetic" as used here is intended to indicate that the CS protein from *P. vivax* occurring in its natural state is specifically excluded from this invention. "Synthetic", as used here, is not intended to preclude production of AGDR (SEQ ID NO:1)-based vaccines by biological methods including, for example, chemical synthetic and DNA recombinant techniques.

Having described the invention, the following examples are given to illustrate specific applications of the invention including the best mode now known to perform the invention. These specific examples are not intended to limit the scope of the invention described in this application.

EXAMPLE 1

The AGDR (SEQ ID NO:1)-based molecules of this invention are produced by chemical synthesis, using the peptide synthesis technology based on, but not limited to that developed by Merrifield (Merrifield, J. Amer. Chem. Soc., 85:2149 (1963)). In the present invention, the synthesis is initiated by condensing the first amino acid onto a solid matrix by an esterification reaction between the activated carboxyl group of the amino acid and the linker attached to the solid matrix. This step is performed in an aliphatic solvent such as N,N-dimethylformamide (DMF). The α-amino groups of all amino acids used in this synthesis are protected by either tert-butyl-oxy-carbonyl (t-Boc) or fluorenyl-methyl-oxy-carbonyl (Fmoc) groups. Fmoc chemistry is preferred. This protective group is removed, in the case of Fmoc chemistry, by treatment with a 20% piperidine solution in DMF. After deprotection, the next amino acid is added. This is accomplished by condensing the second amino acid onto the first by means of an acylation reaction between the acid group on the first amino acid and the deprotected α-amino group on the second amino acid in an inert organic solvent, such as DMF, and in the presence of with a catalyst, such as 1-hydroxybenzotriazole (HOBT). These reactions are carried out at room temperature. Any of the amino acids can be added in any sequence desired. In this invention, the amino acids were added in such an order to create the peptide AGDR (SEQ ID NO:1).

The completed peptide is removed from the matrix by known techniques of acid hydrolysis; in this invention, hydrofluoric acid was used. Once hydrolysed free of the matrix, the peptides repeatedly washed in water and then concentrated to dryness, redissolved in water and freeze-dried. This peptide was then purified by dissolving it in water and subjecting it to gel filtration chromatography over a Sephedex G-25 resin eluted with 0.1M $CH_3COOH$. The major peak was collected and freeze-dried.

EXAMPLE 2

Many vaccines based on the tetrapeptide AGDR (SEQ ID NO:1) can be synthesized. This includes but are not limited to single AGDR (SEQ ID NO:1) molecules, straight chains of repeating AGDR (SEQ ID NO:1) sequences such as $(AGDR)_3$ (SEQ ID NO:1) and $(AGDR)_6$, and branched chain polymers consisting of $(AGDR)_3$ and $(AGDR)_3$ (SEQ ID NO:1) plus a known T-cell helper site. The helper T-cell peptide may be, but is not restricted to, the sequence EYLDKVRATVGTEWTPCSVT (SEQ ID NO:3). These branched chain vaccines are known as MAPS (multiple antigen peptide systems). The basic peptide chains are synthesized according to Example 1. The synthesis of branched chains and the combination of chains containing two different epitopes is accomplished in accordance with the procedures described by Tam and Lu (Tam et al., PNAS, 86:9084 (1989)).

EXAMPLE 3

The present invention can be delivered by injection or other known means to subjects in a variety of ways. Some of these techniques and dosage ranges are described in U.S. Pat. Nos. 4,693,994 and 4,466,917. For administration, they may be coupled to carrier proteins including but not restricted to tetanus toxoid and cholera toxin. The above described molecules can be absorbed to alum (aluminum hydroxide) and delivered parenterally in an aqueous solution. They can also be solubilized in other adjuvants including but not restricted to liposomes, squalane and monophosphoryl lipid A and may also contain immunopotentiators such as bacterial cell wall and cytoskeleton.

EXAMPLE 4

The 8-residue peptide (AGDR)$_2$ (SEQ ID NO:1) is synthesized by the stepwise solid-phase method of Merrifield, R. B; Solid phase peptide synthesis. I. The synthesis of a tetrapeptide; J. Am. Chem. Soc., 85:2149–2154 (1963). Pam-t-Boc-L-arginine (Tos) resin (0.5 nmole) is used as the starting point of the synthesis. The protected peptide resin is deprotected by hydrogen fluoride/p-cresol (9:1, v/v for 1 hour at 0° C.).

EXAMPLE 5

The six repeat peptide (AGDR)$_6$ (SEQ ID NO:1) was synthesized by the methods of Merrifield supra and conjugated to keyhole limpet hemocyanin (KLH) by the method of Staros et al., Anal. Biochem., 156:220 (1986). This (AGDR)$_6$(SEQ ID NO:1)-KLH complex was mixed in a 1:1 emulsion of complete Freund's Adjuvant and water achieving a final concentration of 100 µg/ml of (AGDR)$_6$ (SEQ ID NO:1)-KLH. Each mouse received four 200 µg intramuscular immunizations at two week intervals. Sera collected three (3) weeks after the fourth immunization were tested in ELISA against P. vivax protein and in an immunofluorescent antibody assay against P. vivax sporozoites. In ELISA, all four serum samples reacted very well with (AGDR)$_6$ (SEQ ID NO:1) and a recombinant P. vivax sporozoite protein (NS1$_{81}$V$_{20}$). All four serum samples were also highly reactive with sporozoites in the immunofluorescent antibody assay.

Serum samples from human volunteers living in an area of P. vivax malaria transmission (Flores, Indonesia) were tested for reactivity in ELISA to P. vivax antigens including (AGDR)$_6$ (SEQ ID NO:1). Low but detectable levels of AGDR (SEQ ID NO:1) antibody were detected in 14.2% of the 176 volunteers studied.

The details of the study are described in the next example. A Plasmodium vivax circumsporozoite protein epitope bound by a protective monoclonal antibody has low immunogenicity.

Discussion and Interpretation

The work of Charoenvit et al. (Science, 251:668 (1991)) and the work disclosed here provides scientific evidence for a protective agent against P. vivax sporozoite which may function as a vaccine. It is clear that humans exposed to P. vivax sporozoites under conditions of natural transmission develop antibodies to AGDR (SEQ ID NO:1). Mice immunized with P. vivax sporozoites produce an antibody (NVS3) that reacts with P. vivax sporozoites. When passively transferred, NVS3 protects naive animals from infection with P. vivax sporozoites. NVS3 reacts with AGDR (SEQ ID NO:1), an amino acid sequence in the P. vivax circumsporozoite protein. A molecule consists of six tandem copies of AGDR (SEQ ID NO: 1) conjugated to a carrier protein and mixed with an adjuvant induced antibodies in mice. These antibodies bind to AGDR (SEQ ID NO:1) bind to recombinant copies of the P. vivax circumsporozoite protein, and bind to whole P. vivax sporozoites. It is shown that antibodies to AGDR (SEQ ID NO: 1) protect against P. vivax malaria and that (AGDR)$_6$ (SEQ ID NO:1) can induce antibodies that react with AGDR (SEQ ID NO:1) and with whole P. vivax sporozoites. There is no assay or test other than actual vaccine trials in humans or nonhuman primates that will predict the protective capacity of any given P. vivax malaria vaccine candidate. Short of that, the work described provides compelling evidence that AGDR-based molecules form the basis of a P. vivax sporozoite vaccine.

EXAMPLE 6

A recent study(1) demonstrated that Saimiri monkeys passively immunized with a monoclonal antibody designated NVS3 were protected upon intravenous challenge with $10^4$ Plasmodium vivax sporozoites. NVS3, the antibody used in the original isolation of the P. vivax circumsporozoite (CS) protein gene,(2) was analyzed by peptide mapping. NVS3 binds specifically to the four amino acid sequence AGDR (SEQ ID NO:1) (alanine-glycine-aspartic acid-arginine)(1) which is contained within the repeat region of the circumsporozoite protein of several strains of P. vivax(2–4). When Saimiri monkeys were immunized with NS1$_{81}$V$_{20}$, a peptide vaccine containing 20 copies of the repeat sequence of the P. vivax CS protein, they made a good antibody response to P. vivax sporozoites and to VIVAX-1, another P. vivax CS protein-based vaccine(5). When serum samples from these monkeys were tested in ELISA for activity to (AGDR)$_2$ (SEQ ID NO:1), however, no activity was detected(1) even though multiple copies of AGDR (SEQ ID NO:1) are present in the peptide sequence of NS1$_{81}$V$_{20}$. The experiments just described reveal an interesting problem. A monoclonal antibody to an epitope on the CS protein provides protection when passively transferred to primates one hour before sporozoite challenge. However, an immunogen containing the protective epitope induces an antibody response in primates to the CS protein but does not induce an antibody response to the one P. vivax CS protein epitope known to mediate protective immunity. The current studies were designed to determine whether this failure is peculiar to the vaccine or whether natural exposure to P. vivax sporozoites, as seen in residents of malarious areas, stimulates a response to the epitope AGDR (SEQ ID NO:1).

Materials and Methods

Study Population: The study population consisted of 176 volunteers from the village of Robek, Flores (Lesser Sunda Islands), Indonesia (8° 17'S, 120° 24'E)(6,7). The subjects ranged in age from 0.8 to 78 yrs; 48.3% were male. In May of 1984, 2.5 months after the end of peak malaria transmission season, venous blood samples were obtained from the subjects, Giemsa-stained thick and thin blood films prepared and the remainder of blood allowed to clot and was then centrifuged. Serum was eluted and stored in liquid nitrogen. Spleen sizes on 109 of the subjects were scored by the method of Hackett(7).

Antigens: Sera from the subjects was tested in ELISA for antibody activity to four antigens from the P. vivax circumsporozoite (CS) protein and one from the P. falciparum CS protein. VIVAX-1 is a recombinant protein containing approximately 60% of the CS protein from the Belem strain of *P. vivax*. It contains the repeat regions (DRA A/D GQPAG)$_{20}$ (SEQ ID NO:4)(9). NS1$_{81}$V$_{20}$ is a fusion protein expressed by *Escherichia coli* and contains 20 copies of the nonapeptide repeat present in the repeat region of the CS protein and 81 amino acids derived from the nonstructural protein gene of influenza A(10). R32tet$_{32}$ is a recombinant protein containing 30 copies of the *P. falciparum* CS protein repeat NANP (SEQ ID NO:5) and two copies of the repeat NVDP and the first 32 amino acids of a tetracycline resistance gene(11). The sequence of the peptide based on the *P. vivax* CS protein gene variant VK247(4) is (ANGAGNQPG)$_3$ (SEQ ID NO:6). The fifth antigen was (AGDR)$_6$ (SEQ ID NO:1). This sequence is a hexamer consisting of four consecutive amino acids found within the repeat sequence of the CS protein of several strains of *P. vivax*(2–4). The control peptide (QGPGAP)$_2$ (SEQ ID NO:7) is the major repeat sequence from the CS protein of the murine malarial parasite *P. yoelii*(12).

ELISA: Antigen (100 µl of 4 µg/ml) was fixed to the bottom of wells in Immunlon II® ELISA plates (Dynatech Laboratories Inc., Chantilly, Va.) by incubation in pH 8.0 Dulbecco's phosphate buffered saline (DPBS) overnight at 4° C. All antigens were run in triplicate. Following antigen fixation, nonspecific binding was blocked by incubation for one hour with DPBS containing 0.1% Tween 20, 1% bovine serum albumin and 1% skim milk. Serum samples were diluted 1:100 in DPBS and incubated in the wells at room temperature for one hour. Secondary antibody was horseradish peroxidase-labelled, affinity purified goat anti-human IgG (Kirkegard and Perry, Gaithersburg, Md.). Substrate was ABTS (2,2'-azino-di[3-ethyl-benzthiazole sulfonate] and hydrogen peroxide). All sera were tested for binding to each of the antigens including (QGPGAP)$_2$ (SEQ ID NO:7). In order to control for the intense nonspecific binding frequently seen with hypergammaglobulinemic sera collected in malarious areas, the optical density (OD) of wells containing (QGPGAP)$_2$ (SEQ ID NO:7) as antigen was subtracted from the optical density obtained with each of the human malaria peptides. From this number, the optical density plus two standard deviations of a negative serum control obtained from a person with no history of exposure to malaria was also subtracted from the experimental peptide optical density; the final value is considered the corrected OD for that antigen. Any value greater than zero is considered positive. NVS3(1) and NYS1(12) (2 µg/ml), monoclonal antibodies with specificities for (AGDR)$_6$ (SEQ ID NO:1) and (QGPGAP)$_2$ (SEQ ID NO:7) respectively, served as positive control antibodies on each plate.

*P. vivax* Variant ELISA: The ELISA for detection of antibody to the *P. vivax*-variant CS protein was conducted as described by Wirtz et al.(13). Sera were screened at a 1:50 dilution using the synthetic peptide capture antigen (ANGAGNQPG)$_3$ (SEQ ID NO:6) and tested against an antigen-free control well. The OD of antigen-free wells were subtracted from the OD of the wells containing the variant antigen. From this number, the mean OD plus two standard deviations of ten negative serum controls from naive persons was also subtracted; the final value is considered the corrected OD for (ANGAGNQPG)$_3$ (SEQ ID NO:6) and any value greater than zero was considered positive.

Mouse Vaccination and Serology: Four BALB/c mice were immunized im with 200 µg of (AGDR)$_6$ (SEQ ID NO:1)-KLH in complete Freund's adjuvant. Three control mice received identical immunizations except for the substitute of PBS for the (AGDR)$_6$ (SEQ ID NO:1)-KLH. All the mice received four immunizations at two week intervals. Sera collected two weeks after the second and fourth immunizations were tested for reactivity in ELISA as described above and at a dilution of 1:20 in an IFA assay to dried *P. vivax* sporozoites (Salvador 1 strain) as previously described(15).

RESULTS

Malaria Endemicity: Malaria prevalence figures and spleen rates are presented in Table 1. These data indicate that at the time of the study, the environment was hyperendemic when judged by spleen rates in both children and adults but mesoendemic when judged by parasite rate.

TABLE 1

Subjects from Robek, Flores, Indonesia
Parasite and Spleen Rates

| | Age Groups[1] | | | | |
|---|---|---|---|---|---|
| | 0–1 | 2–9 | 10–15 | >15 | All |
| n | 5 | 51 | 47 | 73 | 176 |
| *P. falciparum* | 0[2] | 13.7 | 21.1 | 6.8 | 12.5 |
| *P. vivax* | 20 | 11.7 | 8.5 | 0 | 6.3 |
| *P. malariae* | 0 | 0 | 4.2 | 0 | 1.1 |
| Mixed Infections | 0 | 3.9 | 0 | 0 | 1.1 |
| Total Infections | 20 | 29.4 | 34 | 6.8 | 21 |
| Sleen Rate[3] | 50(2)[4] | 84.3(32) | 87.5(24) | 91.1(45) | 87.3(103) |
| AES[5] | 1 | 1.78 | 2.13 | 2.17 | 2.08 |

[1]age in years
[2]percent positive by blood film examination
[3]percent with Hackett spleen score greater than zero
[4]number in parentheses is n for those subjects with spleen score recorded
[5]average enlarged spleen Serology of Robek Population: ELISA results for the Robek population are presented in Table 2. Linear regression analysis of age against corrected OD for each antigen (not shown) indicated that positivity in ELISA for antibody to NS1$_{81}$V$_{20}$, VIVAX-1 and R32tet$_{32}$ showed a weak association between increasing optical density and increasing age (p=0.0014, 0.0015 and 0.016 respectively; r=0.239, 0.237 and 0.18, respectively). The percentage of positive ELISA results increased in each successive age group for NS1$_{81}$V$_{20}$, VIVAX-1 and R32tet$_{32}$ (with the exception of 0–1 year old subjects screened for VIVAX-1). The percent positive NS1$_{81}$V$_{20}$ and R32tet$_{32}$ ELISA results for children (2–9 years old) is significantly lower than the percent of positive adults (p=0.03 and 0.04, respectively, Fisher Exact Test, one-tailed). The maximum corrected OD also increases with each successive age group for each of the three antigens (NS1$_{81}$V$_{20}$, VIVAX-1 and R32tet$_{32}$). Mean corrected OD values for each age group generally, but not in every case, showed an upward trend with increasing age (Table 2). In contrast, the percent of subjects positive for AGDR antibodies does not consistently increase with each successively older age group and the difference between the rate of positivity in children versus adults is not significant (p=0.397, Fisher Exact Test, one-tailed). Also, the maximum and mean corrected OD values within each age group do not increase with age and are an order of magnitude lower than the OD values seen with the other three antigens (Table 2). None of the subjects had detectable antibodies levels to *P. vivax* variant peptide as measured in ELISA.

TABLE 2

Subjects from Robek, Flores, Indonesia
ELISA for Malaria Antigens

|  | Age Groups[1] | | | | |
|---|---|---|---|---|---|
|  | <2(5)[2] | 2–9(51) | 10–15(47) | >15(73) | All(176) |
| $NS1_{81}V_{20}$ | | | | | |
| % + | 0 | 37.2 | 46.8 | 71.2 | 52.8 |
| mean OD ± SE[3] | none | .105 ± .029 | .087 ± .025 | .154 ± .023 | .128 ± .015 |
| maximum OD[4] | −.025 | .409 | .531 | .729 | |
| VIVAX-1 | | | | | |
| % + | 80 | 54.9 | 70.2 | 72.6 | 67 |
| mean OD ± SE | .121 ± .061 | .099 ± .022 | .162 ± .03 | .248 ± .026 | .186 ± .016 |
| maximum OD | .299 | .472 | .681 | .698 | |
| $R32tet_{32}$ | | | | | |
| % + | 0 | 43.1 | 59.6 | 76.7 | 60.2 |
| mean OD ± SE | none | .127 ± .03 | .152 ± .031 | .183 ± .02 | .161 ± .015 |
| maximum OD | −.02 | .541 | .597 | .693 | |
| (AGDR(SEQ ID NO. 1))$_6$ | | | | | |
| % + | 0 | 13.7 | 10.6 | 17.8 | 14.2 |
| mean OD ± SE | none | .032 ± .012 | .027 ± .004 | .039 ± .008 | .035 ± .006 |
| maximum OD | −.022 | .095 | .041 | .089 | |

[1] age in years
[2] number in parentheses is n for that group
[3] mean optical density ± standard error
[4] maximum corrected OD within that group for that antigen; these values already have control serum well OD values plus two standard deviations and control antigen well OD values subtracted from them. Any value greater than zero is considered antibody positive.

Serology of Mice: Sera from mice immunized with (AGDR)$_6$ (SEQ ID NO:1)-KLH reacted well in ELISA with both (AGDR)$_6$ (SEQ ID NO:1) and $NS1_{81}V_{20}$ and with dried *P. vivax* sporozoites in an IFA assay (Table 3).

TABLE 3

Immunization of BALB/C Mice with (AGDR)$_6$
Detection of Serum Reactivity to Sporozoites (SPZ) in IFA Assay
and to (AGDR)$_6$ and $NS1_{81}V_{20}$ in ELISA

|  | After 2 Immunizations | | | After 4 Immunizations | | |
|---|---|---|---|---|---|---|
| Mouse No.[1] | SPZ | (SEQ ID NO. 1) (AGDR)$_6$ | $NS1_{81}V_{20}$ | SPZ | (SEQ ID NO. 1) (AGDR)$_6$ | $NS1_{81}V_{20}$ |
| 1 | − | 1.221 | 0.010 | ++++ | 1.046 | 0.669 |
| 2 | ± | 1.225 | 0.832 | +++ | 1.184 | 1.071 |
| 3 | + | 1.251 | 0.902 | ++ | 1.100 | 0.863 |
| 4 | ++++ | 1.263 | 1.062 | ++++ | 1.099 | 1.072 |
| 5 | − | 0.044 | 0 | − | 0.056 | 0.009 |
| 6 | − | 0.002 | 0 | − | 0.027 | 0.004 |
| 7 | − | 0.053 | 0 | − | 0.040 | 0 |

[1] Mice 1–4 were immunized with (AGDR(SEQ ID NO. 1))$_6$-KLH, mice 5–7 were negative controls.

DISCUSSION

NVS3 is a murine monoclonal antibody which, when passively transferred, protected four of six Saimiri monkeys from a 10$^4$ *P. vivax* sporozoite challenge. The two remaining animals experienced statistically significantly extended prepatency periods compared with controls.[1] This was the first unambiguous demonstration that antibodies alone can protect against the sporozoites of a human malaria. Subsequently, the epitope of NVS3 was identified as the amino acid sequence AGDR (SEQ ID NO:1). This occurred even though copies of AGDR (SEQ ID NO:1) are contained within the sequence of both $NS1_{81}V_{20}$ and VIVAX-1. This raises the question of whether populations naturally exposed to *P. vivax* malaria or naive humans vaccinated with a *P. vivax* sporozoite vaccine containing the sequence makes antibodies against it.

The malaria prevalence data (Table 1) show a substantial level of transmission in Robek and the ELISA results indicate that the human subjects living there have generated antibody responses to components of the CS proteins from both *P. vivax* and *P. falciparum*. These transmission and ELISA data both imply that the subjects received sufficient exposure and that a failure to generate antibodies to a given antigen is not due to insufficient antigen exposure. The absence of serum reactivity with the *P. vivax* variant sequence indicates that the *P. vivax* percent positive outcomes for the age group 2–9 compared to the age group >15 for $NS1_{81}V_{20}$ and $R32tet_{32}$ was statistically significant. This increase with age is apparently a function of increased exposure. The ELISA results for (AGDR)$_6$ (SEQ ID NO:1) were not similar. Although antibodies to AGDR (SEQ ID NO:1) were induced by exposure to sporozoites, the levels and prevalence were low.

The finding that AGDR (SEQ ID NO:1) appears to be a very poor immunogen in a natural setting might be explained if AGDR (SEQ ID NO:1) is not exposed on the surface of the sporozoite. The fact that the monoclonal antibody NVS3 protects monkeys challenged with *P. vivax* sporozoites argues persuasively against this.

The failure of both chronic exposure to sporozoites and vaccination with a subunit vaccine to induce substantive antibody levels to AGDR (SEQ ID NO:1) indicates that it is a poor immunogen when presented in these forms. The fact that mice can generate an antibody response to AGDR (SEQ ID NO:1) as demonstrated by the existence of a monoclonal antibody (NVS3) indicates that at least sporozoites present AGDR (SEQ ID NO:1) to the immune system. When an epitope is accessible to the immune system but little detectable antibody response is mounted against it, the possibility exists that other more immunogenic but nonprotective epitopes on the antigen are inducing the majority of immune response. Such a phenomenon would permit the existence of a protective epitope on the *P. vivax* CS protein and its failure to induce a protective immune response. This interpretation is supported by the finding that when mice were immunized with $(AGDR)_6$ (SEQ ID NO:1)-KLH in complete Freund's adjuvant, all mice produced antibodies that reacted with $(AGDR)_6$ (SEQ ID NO:1), $NS1_{81}V_{20}$ and, most importantly, produced high levels to *P. vivax* sporozoites (Table 3). This indicates that while AGDR (SEQ ID NO:1) may be a poor immunogen when presented on sporozoites or recombinant CS protein, synthetic vaccines can be constructed which can induce antibodies of the desired specificity. The goal now will be to develop methods for inducing anti-AGDR (SEQ ID NO:1) polyclonal antibodies using immunogens and adjuvants which can be used in humans.

Obviously, many modifications and variations of the present invention are possible in light of the above teachings. It is therefore to be understood that, within the scope of the appended claims, the invention may be practiced otherwise than as specifically.

REFERENCES

1. Charoenvit Y, Collins W E, Jones T R, Millet P, Yuan L, Campbell G H, Beaudoin R L, Broderson J R, Hoffman S L. 1991. Inability of malaria vaccine to induce antibodies to a protective epitope within its sequence. Science 251:668–671.

2. McCutchan T F, Lal A A, de la Cruz V F, Miller L H, Maloy W L, Charoenvit Y, Beaudoin R L, Guerry P, Wistar R, Hoffman S L, Hockmeyer W T, Collins W E, Wirth D. 1985. Sequence of the immunodominant epitope for the surface protein on sporozoites of Plasmodium vivax. Science 230:1381–1383.

3. Arnot D E, Barnwell J W, Tam J P, Nussenzweig V, Nussenzweig R S, Enea V. 1985. Circumsporozoite protein of *Plasmodium vivax*: gene cloning and characterization of the immunodominant epitope. Science 230:815–818.

4. Rosenberg R, Wirtz R A, Lanar D E, Sattabongkot J, Hall T, Waters A P, Prasittisuk C. 1989. Circumsporozoite protein heterogeneity in the human malaria parasite *Plasmodium vivax*. Science 245:973–976.

5. Collins W E, Nussenzweig R S, Ballou W R, Ruebush T K, Nardin E H, Chulay J D, Majarian W R, Young J F, Wasserman G F, Bathurst I, Gibson H L, Barr P J, Hoffman S L, Wasserman S S, Broderson J R, Skinner J C, Procell P M, Filipski V K, Wilson C L. 1989. Immunization of *Saimiri sciureus boliviensis* with recombinant vaccines based on the circumsporozoite protein of *Plasmodium vivax*. Amer. J. Trop. Med. Hyg. 40:455–464.

6. Hoffman S L, Masbar S, Hussein P R, Soewarta A, Harun S, Marwoto H A, Campbell J R, Smrkovski L, Purnomo, Wiady I. 1984. Absence of malaria mortality in villagers with chloroquine-resistant *Plasmodium falciparum* treated with chloroquine. Trans. Roy. Soc. Trop. Med. Hyg. 78:175–178.

7. Hoffman S L, Wistar R, Ballou W R, Hollingdale M R, Wirtz R A, Schneider I, Marwoto H A, Hockmeyer W T. 1986. Immunity to malaria and naturally acquired antibodies to the circumsporozoite protein of *Plasmodium falciparum*. N. Eng. J. Med. 315:601–606.

8. Bruce-Chwatt L J. 1985. |Essential Malariology|. John Wiley and Sons, New York.

9. Barr P J, Gibson H L, Enea V, Arnot D E, Hollingdale M R, Nussenzweig V. 1987. Expression in yeast of a *Plasmodium vivax* antigen of potential use in a human malaria vaccine. J. Exp. Med. 165:1160–1171.

10. Gordon D M, Cosgriff T M, Schneider I, Wasserman G F, Majarian W R, Hollingdale W R, Chulay J D. 1990. Safety and immunogenicity of a *Plasmodium vivax* sporozoite vaccine. Amer. J. Trop. Med. Hyg. 42:527–531.

11. Ballou W R, Hoffman S L, Sherwood J A, Hollingdale M R, Neva F A, Hockmeyer W T, Gordon D M, Schneider I, Wirtz R A, Young J F, and others. 1987. Safety and efficacy of a recombinant DNA *Plasmodium falciparum* sporozoite vaccine. Lancet 1:1277–1281. UI 87227707.

12. Charoenvit Y, Mellouk S, Cole C, Bechara R, Leef M, Sedegah M, Yuan L F, Robey F A, Beaudoin R L, Hoffman S L. 1991. Monoclonal, but not polyclonal antibodies protect against *Plasmodium yoelii* sporozoites. J. Immunol. 146:1020–1025.

13. Wirtz R A, Rosenberg R. Sattabongkot J, Webster H K. 1990. Prevalence of antibody to heterologous circumsporozoite protein of *Plasmodium vivax* in Thailand. Lancet 336:593–595.

14. Rickman L S, Gordon D M, Wistar R, Krzych U, Gross M, Hollingdale M R, Egan J E, Chulay J D, Hoffman S L. 1991. Use of adjuvant containing mycobacterial cell-wall skeleton, monophosphoryl lipid A, and squalane in malaria circumsporozoite protein vaccine. Lancet 337:998–1001.

15. Charoenvit Y, Leef M F, Yuan L F, Sedegah M, Beaudoin R L. 1987. Characterization of *Plasmodium yoelii* monoclonal antibodies directed against stage-specific sporozoite antigens. Infect. Immun. 55:604–608.

What we claim is:

1. An immunogenic composition comprising:
   (a) a pharmaceutically acceptable carrier, excipient or adjuvant and
   (b) a peptide having at least one repeat of the amino acid sequence -A-G-D-R- and which binds to the monoclonal antibody NVS3.

2. The composition of claim 1 wherein said peptide is covalently conjugated to a carrier moiety.

3. The composition of claim 2 wherein said peptide is covalently conjugated to a carrier protein.

4. The composition of claim 1 wherein said peptide is covalently conjugated to an inert non-hindering spacer moiety, such as a moiety within a multiple antigen peptide system (MAPS).

5. The composition of claim 1 wherein said peptide consists of multiple tandem repeats of the amino acid residues -A-G-D-R- (SEQ ID NO:1).

6. The composition of claim 2 wherein said peptide consists of multiple tandem repeats of the amino acid residues -A-G-D-R- (SEQ ID NO:1).

7. The composition of claim 3 wherein said peptide consists of multiple tandem repeats of the amino acid residues -A-G-D-R- (SEQ ID NO:1).

8. The composition of claim 4 wherein said peptide consists of multiple tandem repeats of the amino acid residues -A-G-D-R- (SEQ ID NO:1).

9. The composition of claim 5 wherein said peptide consists of six tandem repeats of the amino acid residues -A-G-D-R- (SEQ ID NO:1).

10. The composition of claim 6 wherein said peptide consists of six tandem repeats of the amino acid residues -A-G-D-R- (SEQ ID NO:1).

11. The composition of claim 7 wherein said peptide consists of six tandem repeats of the amino acid residues -A-G-D-R- (SEQ ID NO:1).

12. The composition of claim 8 wherein said peptide consists of six tandem repeats of the amino acid residues -A-G-D-R- (SEQ ID NO:1).

* * * * *

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal ( x ) PUBLICATION INFORMATION:
        ( H ) DOCUMENT NUMBER: US 5,095,093
        ( I ) FILING DATE: 10-MAR-1992

( x i ) SEQUENCE DESCRIPTION: SEQ ID NO:1:

Ala  Gly  Asp  Arg
    1

( 2 ) INFORMATION FOR SEQ ID NO:2:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal ( x ) PUBLICATION INFORMATION:
        ( H ) DOCUMENT NUMBER: US 5,095,093
        ( I ) FILING DATE: 10-MAR-1992

( x i ) SEQUENCE DESCRIPTION: SEQ ID NO:2:

Gly  Asp  Arg  Ala  Asp  Gly  Gln  Pro  Ala
    1                       5

( 2 ) INFORMATION FOR SEQ ID NO:3:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal ( x ) PUBLICATION INFORMATION:
        ( H ) DOCUMENT NUMBER: US 5,095,093
        ( I ) FILING DATE: 10-MAR-1992

( x i ) SEQUENCE DESCRIPTION: SEQ ID NO:3:

Glu Tyr Leu Asp Lys Val Arg Ala Thr Val Gly Thr Glu Trp Thr Pro
1               5                   10                  15
Cys Ser Val Thr
            20

( 2 ) INFORMATION FOR SEQ ID NO:4:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal ( i x ) FEATURE:
        ( A ) NAME/KEY: Modified-site
        ( B ) LOCATION: 4
        ( D ) OTHER INFORMATION: /product="OTHER"
            / label=x
            / note="x=a/d"

( x ) PUBLICATION INFORMATION:
        ( H ) DOCUMENT NUMBER: US 5,095,093
        ( I ) FILING DATE: 10-MAR-1992

( x i ) SEQUENCE DESCRIPTION: SEQ ID NO:4:

Asp Arg Ala Xaa Gly Gln Pro Ala Gly
1               5

( 2 ) INFORMATION FOR SEQ ID NO:5:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal ( x ) PUBLICATION INFORMATION:
        ( H ) DOCUMENT NUMBER: US 5,095,093
        ( I ) FILING DATE: 10-MAR-1992

( x i ) SEQUENCE DESCRIPTION: SEQ ID NO:5:

Asn Ala Asn Pro
1

( 2 ) INFORMATION FOR SEQ ID NO:6:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO (iv) ANTI-SENSE: NO (v) FRAGMENT TYPE: N-terminal (x) PUBLICATION INFORMATION:
(H) DOCUMENT NUMBER: US 5,095,093
(I) FILING DATE: 10-MAR-1992

(xi) SEQUENCE DESCRIPTION: SEQ ID NO:6:

```
Ala Asn Gly Ala Gly Asn Gln Pro Gly
1               5
```

(2) INFORMATION FOR SEQ ID NO:7:

(i) SEQUENCE CHARACTERISTICS:
(A) LENGTH: 6 amino acids
(B) TYPE: amino acid
(C) STRANDEDNESS: single
(D) TOPOLOGY: linear (ii) MOLECULE TYPE: protein (iii) HYPOTHETICAL: NO (iv) ANTI-SENSE: NO (v) FRAGMENT TYPE: N-terminal (x) PUBLICATION INFORMATION:
(H) DOCUMENT NUMBER: US 5,095,093
(I) FILING DATE: 10-MAR-1992

(xi) SEQUENCE DESCRIPTION: SEQ ID NO:7:

```
Gln Gly Pro Gly Ala Pro
1               5
```